United States Patent [19]

Horn et al.

[11] Patent Number: 4,701,304

[45] Date of Patent: Oct. 20, 1987

[54] APPARATUS FOR AUTOMATED SYNTHESIS OF PEPTIDES

[75] Inventors: Marcus J. Horn, Arlington; William K. Miller, Sharon, both of Mass.

[73] Assignee: Applied Protein Technologies, Inc., Cambridge, Mass.

[21] Appl. No.: 725,213

[22] Filed: Apr. 19, 1985

[51] Int. Cl.$^4$ .................. B01J 14/00; G01N 33/68
[52] U.S. Cl. .................................. 422/62; 422/81; 422/108; 422/111; 422/129; 422/131; 422/211; 422/100; 422/102; 435/287; 436/89; 935/87; 935/88; 536/27
[58] Field of Search .......................... 222/129, 144.5; 260/112.5 R; 422/62, 71, 81, 108, 111, 113, 116, 129, 131, 211, 189, 224, 228, 234, 231, 100, 101, 103; 435/287, 288, 289; 436/55, 89, 90, 161, 94; 935/87, 88; 536/27

[56] References Cited

U.S. PATENT DOCUMENTS

| | | | |
|---|---|---|---|
| 2,383,946 | 9/1945 | Tietig | 422/231 |
| 3,531,258 | 9/1970 | Merrifield et al. | 422/116 |
| 3,540,982 | 11/1970 | Sepall | 422/116 |
| 3,557,077 | 1/1971 | Brunfeldt et al. | 422/108 |
| 3,647,390 | 3/1972 | Kubodera et al. | 422/116 |
| 3,701,634 | 10/1972 | Worden | 422/130 |
| 3,725,010 | 4/1973 | Penhasi | 436/89 |
| 4,153,416 | 5/1979 | Bonner et al. | 422/71 |
| 4,353,989 | 10/1982 | Bender et al. | 435/287 |
| 4,362,699 | 12/1982 | Verlander et al. | 422/116 |
| 4,458,066 | 7/1984 | Caruthers et al. | 536/27 |
| 4,477,578 | 10/1984 | Miles et al. | 422/68 |
| 4,483,964 | 11/1984 | Urdea et al. | 422/116 |
| 4,517,338 | 5/1985 | Urdea et al. | 422/116 |

OTHER PUBLICATIONS

Biosearch—*Sam Two Peptide Synthesizer* (brochure).
Applied Biosystems—*430A Peptide Synthesizer* (brochure).
Peptides International Excellence Compounded—*Syn–Thor 2000* (brochure).
Vega Biotechnologies—*Vega Coupler 1000, 296* (brochures).
Labortec—*Peptide Synthesizer SP 640* (advertisement).
CRB *Pepsynthesiser* (brochure).
The Peptide Synthesizer *System 990* (brochure).
G. Barany & R. B. Merrifield, *The Peptides*, V2, 1979, Academic Press.
R. S. Hodges & R. B. Merrifield, *Analytical Biochemistry* 65, 241–272 (1975).
W. S. Hancock, J. E. Battersby, and D. R. K. Harding, *Analytical Biochemistry* 69, 497–503 (1975).
M. D. Matteucci & M. H. Caruthers, *Synthesis of Deoxyoligonucleotides on a Polymer Support*.
Proteins: Covalent Backbone and Amino Acid Sequence—*Laboratory Synthesis of Polypeptide Chains* (Chapter 5).

Primary Examiner—Michael S. Marcus
Attorney, Agent, or Firm—Cesari and McKenna

[57] ABSTRACT

A system maintained under a constant reference pressure for the automated synthesis of peptides includes a reaction vessel that has a single port for both injection and withdrawal of the various fluids used in the peptide synthesis sequence, a plurality of reservoirs for holding the amino acids used in the synthesis of the peptide chains and a plurality of reservoirs for holding the solvents and reagents used to promote the synthesis of the peptide chains. The system also includes a volume displacement pump for removing a controlled volume of gas from the reaction vessel as the first part of each injection step to reduce the pressure within the vessel. This is followed by connection of a selected reservoir to the reaction vessel and flow from the reservoir to the vessel resulting from the pressure differential between the vessel and the reservoir. As soon as the pressure in the reaction vessel has returned to reference level, the transfer is complete.

Because all parts of the system are maintained at the reference pressure, metered transfer of reagents and solvents from the reservoirs to the reaction vessel can be performed easily without using a high vacuum. Transfer is self-terminating, and is readily controlled. Furthermore, the system easily accommodates wide volume ranges, and lends itself readily to automation.

6 Claims, 2 Drawing Figures

APPARATUS FOR AUTOMATED SYNTHESIS OF PEPTIDES

FIELD OF THE INVENTION

This invention relates to a method and apparatus for automating the manufacture of a substance involving a sequence of chemical reactions, and more particularly to a system for the synthesis of organic compounds, such as peptides and proteins. The invention is especially suited to the solid-phase synthesis of peptides.

BACKGROUND OF THE INVENTION

The solid-phase synthesis of a peptide involves stepwise additions of amino-terminus-blocked amino acids to a peptide chain, the carboxyl terminus of which is anchored to a solid support. The synthesis begins with the amino acid at the carboxyl-terminal of the chain and proceeds with single- amino acid additions to the successive amino termini of the chain. It is initiated by covalently attaching the carboxyl terminus of the carboxyl-terminal amino acid to an insoluble solid support, which is typically a matrix of resin beads that are large enough to be separated from the liquid phase by filtration.

The next amino acid to be added is first protected at its amino terminus with a blocking group so that this terminus is no longer reactive with the reagents that promote the formation of peptide bonds. The blocked amino acid is then reacted, in the presence of a condensing agent, such as dicyclohexyl-carbodiimide, with the anchored amino acid to form a peptide bond between the carboxyl terminus of the blocked amino acid and the amino terminus of the anchored amino acid.

The resulting peptide chain (which now consists of two amino acids) remains anchored to the insoluble resin, and is therefore easily separated from the reactants by thorough washing. The blocking group is then removed from the amino terminus of the amino terminal amino acid of the peptide chain by acidification so that the peptide is now terminated with a free amino group that is ready to react with the next blocked amino acid to be added to the chain.

In similar fashion, subsequent amino acids are added to the anchored peptide chain to build the complete peptide. After the peptide is completed, it is removed from the insoluble resin and isolated.

In reality, peptide synthesis is more complicated. For example, the reagents used to form the peptide bond also react with side groups of some of the amino acids (approximately twenty different amino acids are routinely used to form a peptide). Therefore, these sensitive side groups must also be protected with special blocking groups during the entire synthesis of the peptide. These special blocking groups must be stable under the conditions of deblocking of the amino-terminal termini of the peptide chains and must also be readily removed from the completed peptide.

Also, each amino acid has its own individual optimum reaction kinetics, and these kinetics are affected by the environment surrounding the amino terminal of the peptide chain. This environment is determined not only by the amino acid at the amino terminus itself, but also by the other amino acids in the peptide chain and their interactions with both the solid and the liquid phases.

Specifically, the different amino acid configurations may cause the peptide to bend and fold three-dimensionally, and thus the free amino terminus of the amino terminal may be hindered sterically from reacting with the blocked amino acid to be added to the peptide chain. Also, the different amino acids in the chain have different hydrophobic/hydrophilic effects on the surroundings of the free amino terminal, particularly on the solvation of the resin itself, which affect the accessibility of the free amino terminus to the liquid reactants and, thus, the reaction rate. Therefore, since the sequence of each peptide to be synthesized is different, the optimum reaction conditions for each amino acid addition are difficult to predict.

As a result, the reaction at each step of the synthesis seldom goes to completion, that is, the yield is generally somewhat less than 100%. Obviously, the yield at each step must be very high if a peptide chain of substantial length is to be prepared in substantial quantity. For example, a yield of 99.0% per step results in a product yield of only 81% after 20 amino acid additions, while a yield per step increase of only 0.5% (to 99.5% per step) results in a product of 90% yield—almost 10% higher. Another increase of only 0.4% per step—to 99.9% results in a 98% ultimate yield. The yield represents not only the total amount of the resulting peptide, but also its purity. The purity is important because it is difficult and costly to separate the desired peptide from undesired peptides that vary in only a few amino acids, and which arise from incomplete reactions. The total amount is important because if the yield is low, the amount of expensive starting materials must be increased accordingly.

A system for synthesizing these peptides must therefore accomodate the large number of different steps and the varying reaction conditions. It also must be constructed to minimize cross-contamination among the amino acids, as well as the solvents and reagents used in the process. Ideally, the system should further include a method for monitoring the completeness of each amino acid addition before the next amino acid is added to the peptide chain. Such a system ensures the highest possible yield at each step.

Prior apparatus for synthesizing peptides can be divided into two types: column synthesizers, such as described in U.S. Pat. No. 4,362,699, and shaker/reactor vessels, which are described in the U.S. Pat. Nos. 3,531,258, 3,647,390, and 3,557,077.

In the column synthesizers, solid support beads to which the growing peptide chains are attached are packed into a column. The reagents, solvents, and amino acids required for synthesizing the peptide are reacted with the solid support by passing them sequentially through the column. To obtain reasonable flow rates, these column synthesizers are operated under high pressure, usually greater than 200 psi. With unidirectional flow through the column, the high pressure may compress the solid supports, thus causing increased back pressure and pumping problems. These pressure problems require that special precautions be taken in the system design.

The prior shaker/reactor systems contain filters made from glass frits for retaining a particulate insoluble matrix in a reactor vessel while allowing passage of liquid and gas. Generally, these reactor vessels have separate inlets and outlets for unidirectional flow through the reactor and its filter, such as described in U.S. Pat. No. 3,557,077 to Brundfeldt et al.

During the various intermediate steps required for each amino acid addition, the different solvents cause the solid support to swell and shrink. The shrunken beads may enter the pores in the filter during one step, and swell during a subsequent step, thereby trapping the beads in the filter. Since flow through the filter is unidirectional, the trapped beads are not removed from the filter, and eventually, during the course of peptide synthesis, they accumulate in sufficient quantity to impede flow through the filter. Also, clogging of the filter makes the trapped beads at least partially inaccessible to the reaction solvents and reagents, resulting in incomplete reactions at each step.

In the Merrifield U.S. Pat. No. 3,521,258, this clogging of the filter causes a backpressure buildup in the system that makes it difficult to obtain a closely metered flow into the reactor. Close metering is important because, with an increase in the degree of uncertainty in the transfer, a corresponding increase in the amount of expensive reagents which must be transferred to compensate for this uncertainty.

There are other drawbacks in these prior systems. For example, in the Merrifield et al., U.S. Pat. No. 3,521,258, cross-contamination between solvents and reagents in the selector valves and pumps is a problem. Also, this device cannot accomodate a wide range of reaction volumes because the metering pump is adjustable only over a relatively narrow volume range. Thus, it cannot be used to produce both analytical (small) and commercial (large) quantities of peptides.

Kubodera et al., U.S. Pat. No. 3,647,390, describes a system that avoids clogging of the filter. The reaction vessel has a single port for both inflow and outflow. There is a single filter between this port and a reaction chamber. Thus each time liquid ingredients or reagents are added to the vessel, their flow through the filter tends to dislodge matrix beads that were retained on the filter during the preceding removal of liquid from the vessel. In Kubodera et al., liquid from the reservoirs is transferred to an intermediate metering vessel, and subsequently, from the intermediate metering vessel to the reaction vessel. The metering is accomplished by drawing a vacuum on a vacuum chamber, and connecting the chamber to the intermediate metering vessel. The resulting pressure decrease in the intermediate metering vessel causes transfer of liquid from the reservoir to the intermediate metering vessel until the pressure in the intermediate metering vessel and the vacuum chamber increase to standard pressure. Thus the amount of liquid transferred is directly related to the volumes of the intermediate metering vessel and the vacuum chamber.

This system is cumbersome in that a significant and high vacuum must be drawn on the vacuum chamber for accurate metering of the various liquids. Also, it is difficult to vary the amount drawn to cope with different size reaction vessels, or different quantities or amounts. Essentially, one must change to different-size vacuum chambers. This system also presents a significant likelihood of cross-contamination in the intermediate metering vessel, because it is difficult to completely remove the various liquids from the walls of the intermediate metering vessel before subsequent liquids are introduced.

SUMMARY OF THE INVENTION

Accordingly, the invention aims to provide a shaker/reactor type system for automated synthesis of peptides which accurately meters flow of the various liquids into the shaker/reactor.

Another object of the invention is to provide such a system which is adaptable to metering different quantities of different reagents.

Yet another object of the invention is to provide such a system wherein the reagents, solvents and amino acids may be sequentially transferred to a reaction vessel with minimal cross-contamination.

A further object of the invention is to provide a system which can accommodate synthesis of both large and small quantities of peptides.

A still further object of the invention is to provide a such a system wherein each step of the reaction is monitored for degree of completion.

Other objects will, in part, be obvious and will, in part, appear hereinafter.

The invention broadly comprises a system maintained under a constant reference pressure, and including a reaction vessel that has a single port for both injection and withdrawal of the various fluids used in the peptide synthesis sequence. The system also includes a volume-displacement pump, specifically a piston-type syringe, for decreasing the pressure in the reaction vessel by removing a controlled volume of gas from the reaction vessel as the first part of each injection step to reduce the pressure within the vessel. This is followed by connection of a selected reservoir to the reaction vessel and flow from the reservoir to the vessel resulting from the pressure differential between the vessel and the reservoir. As soon as the pressure in the reaction vessel has returned to the equilibrium reference level, the transfer is complete.

Removal of a controlled volume of gas from the reaction vessel does not require the evacuation of a chamber and thus can be performed easily without using a high vacuum. The amount of liquid tranferred is easily adjustable to accomodate different amounts of selected reagents as well as to accomodate synthesis of different peptide quantities. Transfer is performed directly into the reaction vessel without the use of an intermediate chamber. Thus, the transfer system is easily cleaned to prevent cross-contamination between amino acids, solvents and reagents. Moreover, it lends itself to automatic operation. This is important in peptide synthesis because it takes several hours of reaction time to add even one amino acid to the chain.

For a fuller understanding of the nature and objects of the invention, reference should be had to the following detailed description, taken in connection with the accompanying drawing figures.

DESCRIPTION OF THE PREFERRED EMBODIMENT

Figure 1:
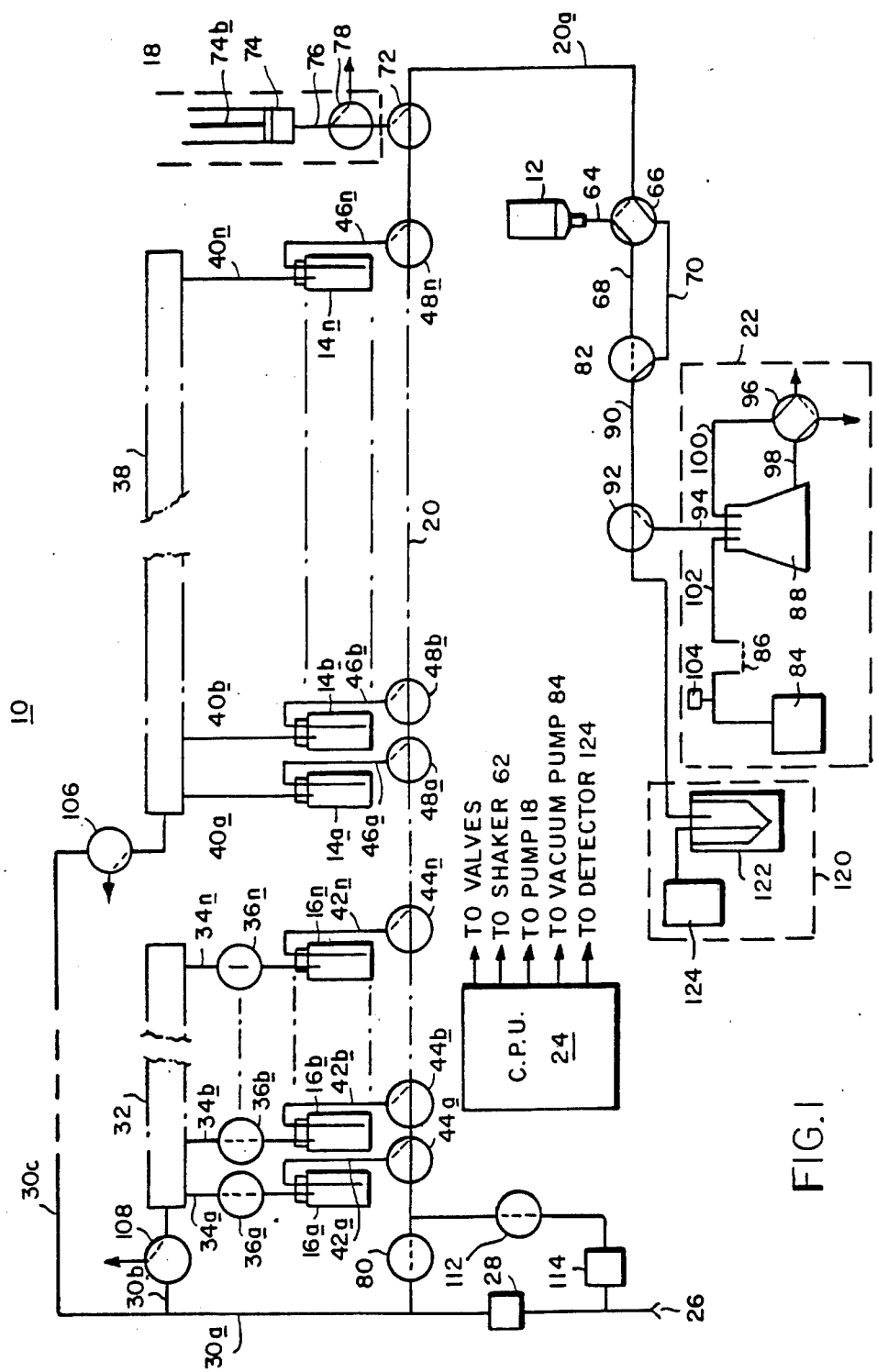
FIG. 1 is a schematic drawing of the overall apparatus embodying the invention.

Referring to FIG. 1, a system 10 for synthesizing peptides broadly comprises a reaction vessel 12 in which the peptide chains are manufactured; a plurality of amino acid reservoirs 14a–14n, each containing an amino acid Aa–An, the "building-block" subunits of the peptide; a plurality of reagent reservoirs 16a–16n, each containing a solvent or reagent Ra–Rn for promoting the synthesis of the peptide; a volume displacement pump 18 for removing predetermined volumes of gas from the vessel 12; a main transfer line 20 for transferring reagents and amino acids from the reservoirs to the reaction vessel; an exhaust system 22 for removing gaseous and liquid wastes from the vessels and the transfer line; and a central processor 24, which controls operation of the various components of the system.

All parts of the system that contact the reagents and solvents are made of chemically resistant materials, such as teflon, glass, or stainless steel.

A reference pressure P is supplied to the system by a nitrogen pressure source 26 and a pressure regulator 28. This pressure P is typically 2–5 p.s.i., but can be set to any pressure, preferably above atmospheric. It is applied from source 26 to reservoirs 16a–16n through lines 30a and 30b, which feed into a manifold 32. The manifold 32, in turn, connects to the reservoirs 16a–16n through a plurality of lines 34a–34n. The lines 34a–34n are further equipped with corresponding valves 36a–36n. These valves 36a–36n, in their normal or deactuated connections, close the reservoirs to the manifold 32 and the pressure source 26. During pressurization of the reservoirs 16a–16n, valves 36a–36n are actuated and deactuated independently to equilibrate selected reservoirs with the pressure P. The independent valve actuation isolates each of the reservoirs and thereby prevents cross-contamination which would result from backflow of volatile reagents Ra–Rn to the manifold if the reservoirs were all connected to the manifold 32 at the same time.

The valves 36a–36n, as well as the other valves in the system 10, are pneumatically- rather than electrically-actuated to prevent chemically-induced corrosion of the valves by the liquids transferred therethrough. The normal, or deactuated connections of the valves are represented in the drawing as solid lines, and the actuated connections of the valves are represented as dotted lines. Pressure for the operation of the pneumatically-actuated valves is supplied by the pressure source 26, under separate regulation, and is controlled by individually electrically-energized actuators (not shown).

Similarly, the reference pressure P is applied to the amino acid reservoirs 14a–14n through lines 30a and 30c, and a second manifold 38. Manifold 38 connects to the reservoirs 14a–14n through lines 40a–40n, respectively. The lines 40a–40n are not equipped with valves similar to the valves 36a–36n, because amino acids are not volatile, and consequently there is little danger of cross-contamination from volatiles backflowing into the manifold 38.

The reservoirs 16a–16n are connected to the main transfer line 20 through corresponding branch lines 42a–42n and valves 44a–44n. Similarly, the reservoirs 14a–14n are connected to the main transfer line 20 through corresponding branch lines 46a–46n and valves 48a–48n. The valves 44a–44n and 48a–48n are connected in series along main transfer line 20, with their normal connections being "open" along main line 20 and "closed" to their respective reservoirs 16a–16n and 14a–14n.

Figure 2:
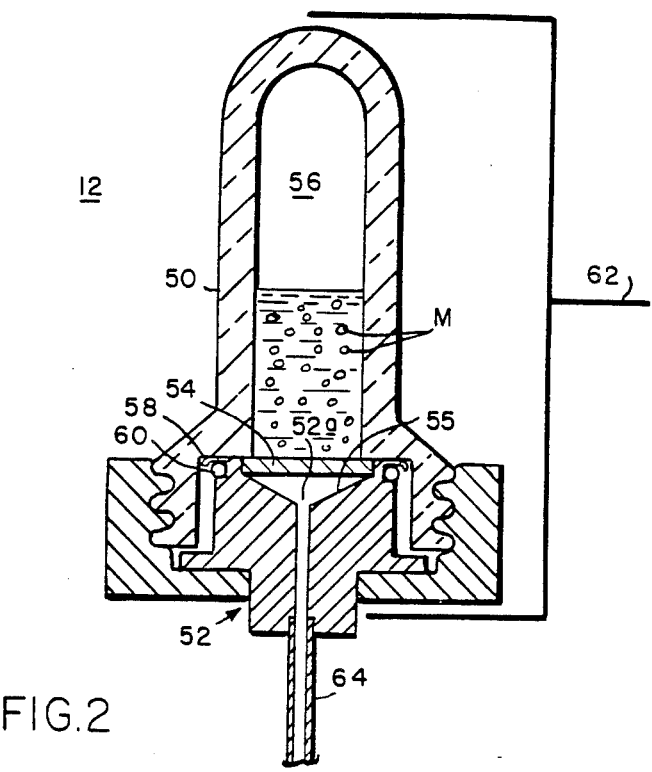
FIG. 2 is a sectional view of the reaction vessel used in the apparatus of the invention.

The reaction vessel 12 is shown in more detail in FIG. 2. It comprises an upper section 50, threaded to a lower section 52. Lower section 52 has a single port 52a, and houses a porous filter 54 extending across the vessel 12 and thus across the port 52a. With the upper section 50, the filter 54 defines a reaction chamber 56. The chamber 56 encloses an insoluble support matrix M, typically in the form of polystyrene or other resin beads, to which is attached the carboxyl-terminal amino acids of the peptide chains to be built. Gas and liquid flow into and out of the chamber 56 through port 52a and filter 54.

More specifically, the filter 54 fits snugly within a preformed well 55 in the lower section 52. The well 55 is tapered towards the port 52a to ensure communication between the port and the under surface of the filter 54. A seal is provided by a gasket 58 and a resilient O-ring 60. When the upper section 50 is threaded to lower section 52, a shoulder 50a fits tightly against the gasket 58, and compresses the O-ring 60. This tightens the O-ring around the filter 54 to hold the filter securely in place during flow therethrough into the chamber 56.

The insoluble support matrix M to which the peptide chains are anchored is typically made from a resin such as polystyrene or polyacrylamide, but it may also be made of any other suitable material, such as acrylamide-impregnated silica or porous glass, to which the peptide chains may be attached but which is otherwise inert in the context of the reactions carried out in the vessel 12.

The porosity of filter 54 is such that it retains the matrix M within the chamber 56, while allowing passage of liquid and gas through the filter 54 into and out of the chamber 56. Thus, the matrix M, and its anchored peptide chains, can be easily separated by the filter from the liquid and gaseous reactants and by-products involved in the processes that take place in the vessel 12.

The vessel 12 is further equipped with a shaker 62, shown schematically in FIG. 2, for slow reciprocation through an angle of approximately 180°, so that the matrix M beads, and the peptide chains attached to them are throughly mixed with the liquid solvents, reagents or amino acids in the chamber 56. The beads of matrix M can become "sticky" in some of the organic solvents used, and resultantly adhere to the walls of chamber 56. Therefore, in order to ensure that all beads of the matrix M, including beads that are stuck to the chamber wall, come in contact with the liquid reactants of each step of the overall process, vessel 12 is sized such that its total volume capacity is less than twice the liquid reaction volume. This allows all of the matrix beads, including beads stuck to the walls of the chamber to contact the liquid reactants in the vessel during each shaking cycle.

Returning to FIG. 1, the vessel 12 is connected to the other parts of the system 10 through its port 52a by a flexible transfer line 64 and a valve 66. When actuated, valve 66 connects the reaction vessel 12 solely to the main transfer line 20. When deactuated, valve 66 forms dual connections: it connects the reaction vessel 12 with a waste removal line 68, and, at the same time, it connects the main transfer line 20 with a second waste removal line 70 which bypasses reaction vessel 12.

Transfer of solvents, reagents, and amino acids from the reservoirs 16a–16n and 14a–14n to the reaction vessel 12 is accomplished by the volume displacement pump 18, which taps directly to main transfer line 20 through a valve 72. Valve 72 has its normal connection closed to pump 18 and open along transfer line 20. Pump 18 comprises a rigidly mounted syringe 74 having a plunger 74b attached to an actuator. The syringe 74 has a single port 74a connected to the valve 72 by a line 76 and a valve 78.

To begin a transfer, the system 10 is equilibrated to the reference pressure P. The vessel 12 is pressurized to the reference pressure through line 20 by actuating the valve 66, and also a valve 80 that connects the main transfer line 20 to the reference pressure from source 26. The valve 80 is then deactuated. At this time, the pump 18 is at its is at its zero-position, with the syringe plunger 74b at its lower most position.

Next the valve 72 is actuated so that the interior of the syringe 74 and the vessel 12 communicate with each other through the valve 66 and the portion 20a of the line 20 between them. Then the plunger 74b is withdrawn to a predetermined volume. This withdrawal increases the effective volume of the vessel 12 in the amount of the volume within the syringe, and, thus, lowers the pressure in the vessel 12.

Transfer of a selected amino acid, e.g. amino acid Aa in reservoir 14a, is then effected by deactuating the valve 72, and actuating the valve 48a, thus connecting the selected reservoir 14a to the vessel 12. The pressure returns to equilibrium by transferring a volume of liquid Aa from the reservoir 14a to the vessel 12.

There is a simple relationship betwen the displacement of the pump 18 and the volume of liquid transferred to the reaction vessel 12. Assume, for example, that the plunger 74 is displaced from its zero-volume position to a point where the volume in the syringe equals the gas volume of the vessel 12. Then, neglecting the small volume in the portion 20a of line 20 between the pump 18 and the vessel 12, one-half the gas in the vessel 12 will transfer to the pump 18. This is equivalent to evacuating one-half the vessel 12 and maintaining the other half at its original, i.e. reference, pressure. Accordingly, when a reservoir is then connected to the vessel 12, the quantity of liquid transferred to the vessel 12 is one-half the volume of the vessel.

Similarly, if the volume displacement of the pump 18 is one-half the gas volume of the vessel 12, the gas in the vessel 12 will divide between the vessel 12 and the pump 18 in the ratio 2:1, i.e., one-third of the gas in the vessel 12 will transfer to the pump 18. Accordingly, the volume of liquid subsequently transferred from a reservoir will be one-third the gas volume of the vessel 12.

Greater accuracy in liquid transfers to the vessel 12 can be obtained by accounting for the zero-position volume of the pump 18, i.e. between the valve 72 and the bottom of the plunger 74b in its lower most position, the volume of the line portion 20a and the portion of the line 20 between the selected reservoir and the valve 72. The volume of the line portion 20a and the zero-position volume of the pump 18 can be considered as part of the gas volume of the vessel 12 in calculating the stroke of the pump 18.

On the other hand, the gas in the line 20 portion between the selected reservoir and the valve 72 is transferred to the vessel 12 in advance of the liquid. Accordingly, since this gas is at the reference pressure immediately prior to the transfer from that reservoir, the volume of this portion of the line 20 should be added to the volume of liquid to be transerred in calculating the stroke of the pump 18.

Additionally, when the vessel 12 reaches pressure equilibrium at the end of a liquid transfer, the transfer line portion 20a will contain some of the liquid retrieved from the selected reservoir. A valve 112, which taps into the line 20 between the valve 80 and the reservoir valves 44a–44n, and which connects the line 20 to the pressure source 26 at a point before the pressure regulator 28, is therefore actuated to apply an elevated pressure to the line 20 to force this liquid into the vessel 12. This elevated pressure is regulated by a second pressure regulator 114.

The valve 66 is then deactuated, closing the vessel 12 to the main line 20 and, at the same time, shunting the line 20 to the waste removal line 70. When valve 66 is deactuated, vessel 12 communicates directly to one end of the waste removal line 68, which is closed to the system 10 at this time because of a deactuated valve 82 located at the other end of the line 68. At this time (or subsequently), the plunger 74b of the pump 18 is retrieved to its initial (bottom) position. During this displacement of the plunger, the valve 78 is actuated to vent the pump to the atmosphere.

The reaction vessel 12 is then reciprocated by the shaker 62. for a short time so that the liquid amino acid introduced into the vessel 12 mixes with the solid matrix M. Then, the reagents or solvents, for example reagent Ra in reservoir 16a, that are required to promote attachment of the amino acid to the free end of the peptide chain, (or, initially, in the case of the carboxyl-terminal amino acid of chain, to promote attachment of the amino acid to the matrix M) are transferred from the selected reservoir, for example, from reservoir 16a, to the vessel 12.

For this second transfer, (and for any subsequent transfers), the vessel 12 is first turned upside-down so that the gaseous portion of chamber 56 communicates with the port 52a. Then, the vessel 12 is vented to atmospheric pressure to exhaust any increased vapor pressure caused by mixing of the contents of vessel 12. Venting of the vessel 12 occurs through the exhaust system 22, as described below.

The vessel 12 is then equilibrated to the reference pressure P, and a second volume of gas is removed from the vessel 12, by operating the valves 66 and 72 and withdrawing the syringe plunger 74b to the desired displacement volume. Valve 72 is deactuated and the valve 44a is actuated, connecting the selected reservoir 16a to the vessel 12. The pressure differential between the reservoir and the vessel transfers the reagent Ra (a volume proportional to the volume of gas removed from the vessel) from the reservoir 16a to the vessel 12. Then, valve 44a is deactuated, the line 20 is flushed with nitrogen as described previously, and the vessel 12 is shaken for a short time to mix its liquid and solid contents.

Following the above procedure, any further solvents or reagents that may be required for the reaction are added to the vessel 12. Then, the reaction is allowed to proceed by slowly reciprocating the vessel 12 by the shaker 62. After a prescribed period of time for the reaction to occur, the shaker 62 is turned off and the vessel 12 is turned right-side-up so that the liquid portion of the vessel 12 communicates with the port 52a. In this position, the liquid and gaseous contents of the vessel 12 are emptied to the exhaust system 22 by application of a vacuum.

More specifically, the exhaust system 22 broadly comprises a vacuum pump 84, a cold trap 86, and a waste collection receptacle 88. The system 22 connects to the rest of the system 10 at the valve 82, through a line 90 and a connecting valve 92. The valve 92, in its deactuated connection, isolates the exhaust system 22 from the rest of the system 10. When actuated, the valve 92 connects the rest of system 10 to the waste receptacle 88 through a line 94.

The first step for the removal of liquid contents of the vessel 12, is to actuate a valve 96, closing the waste collection receptacle 88 to the atmosphere. Then, the vacuum pump 84 is turned on, and the receptacle 88 is evacuated through a connecting line 102. A bleed/check valve 104, positioned in the line 102, allows only a prescribed level of vacuum in the receptacle 88, as well as parts of the system 10 connected thereto, to prevent damage by excessive vacuum to the vessel 12, and the connecting valves and lines. The bleed/check valve 104 also holds the vacuum in the exhaust system when the pump 84 is turned off.

After the receptacle 88 is evacuated, the vacuum pump 84 is turned off and the valves 92 and 82 are actuated. Thus, the vessel 12 and the receptacle 88 communicate through line 68, actuated valve 82, line 90, actuated valve 92, and line 94. The difference in pressure between the receptacle 88 and the vessel 12 causes the liquid contents of the vessel 12 to be transferred to the receptacle 88. Because the vacuum pump is turned off while the liquid contents are being transferred, volatiles that are drawn off into the receptacle 88 are not drawn into the vacuum pump 84. After emptying the reaction vessel 12, the valve 92 is then deactuated, cutting off the exhaust system 22 from the vessel 12.

Then, valves 80 and 66 are actuated so that the vessel 12 is repressurized to the reference pressure P, and any liquid remaining in the valve 66 is pushed into the vessel 12. After repressurization of the vessel, valves 80 and 66 are again deactuated, and the valve 92 is actuated to connect the the vessel 12 with the exhaust system 22, and the vessel is evacuated for a second time, as described above. This second pressurization and evacuation of the vessel 12 completely and effectively empties the liquid and gaseous contents of the vessel 12. The valve 92 is then deactuated, closing the exhaust system 22 to the system 10, and the vessel 12.

Waste collected in the receptacle 88 is removed by deactuating the valve 96. The deactuated valve 96 forms dual connections. Waste in the receptacle 88 is removed through a line 98 and one of the deactuated valve 96 connections. At this time the receptacle 88 is vented to the atmosphere through a line 100 and the other of the deactuated valve 96 connections.

Thus, any desired combination of reactants (amino acids, solvents, reagents) are easily transferred from the reservoirs to the reaction vessel 12, and the transfer is automatically controlled by the processor 24, by regulating the valves, and the stroke of the volume displacement pump 18. The entire peptide synthesis is processor-controlled by also controlling the vacuum pump in the exhaust system, the shaker 62, and the remaining valves in the system.

A user of the system needs only to enter a desired peptide sequence into the processor 24. Under control of a suitable program, the processor then automatically selects pre-determined appropriate reaction conditions (time, duration, amino acid, solvent or reagent) for each amino acid addition to the peptide, and initiates the appropriate commands, in the appropriate sequence, and at the appropriate times, to obtain these conditions.

The exhaust system 22 also serves to clean the main transfer line 20 by evacuation. For this function, the valves 80 and 92 are actuated, and the vacuum pump 84 is turned on. Thus, the line 20 communicates with the vacuum pump 84 through the deactuated valve 66, the line 70, the deactuated valve 82, the line 90, the actuated valve 92 and the line 94, and the receptacle 88. Liquid remaining in the line 20 is thus collected in the receptacle 88.

Also, as described above, excess pressure can result in the reaction vessel 12 due to the vapor pressure of volatile solvents, and the shaking of the vessel. It can also result from gaseous by-products of some of the reactions required for peptide synthesis. This excess pressure is removed from the vessel 12, by venting it to the atmosphere through the exhaust system 22. Venting is accomplished by deactuating the valve 96, and actuating the valves 92 and 82 while the vacuum pump 94 is turned off. Thus the vessel 12 communicates to the atmosphere through the receptacle 88 and the valve 96. Subsequent repressurization of the vessel to the reference pressure thus allows for exact metering of reagent transfer.

Furthermore, the quantity of reactant transferred from a reservoir to the vessel can be varied easily from transfer to transfer by varying the stroke of the volume displacement pump 18 and thereby changing the volume of gas withdrawn from the reaction vessel 12. Moreover, if the volume to be withdrawn exceeds the capacity of the pump 18 in single-stroke displacement of the plunger 74b, multiple strokes can be used to obtain the desired volume.

Specifically, after the first stroke, the valve 78 is actuated to keep the vacuum in the system and to vent the interior of the pump 18 and the plunger 74b is returned to its zero-volume position. Then, the valve 78 is deactuated and the plunger is withdrawn again. This procedure is repeated as often as is necessary to withdraw the desired volume from the vessel 12. Thus, using muliple strokes of the pump, a single syringe of small volume, can be used to withdraw large volumes. Also, the same syringe can be used to withdraw both large and small volumes at will.

To refill or replace one of the reservoirs 14a–14n, a valve 106, positioned in the line 30c, is actuated. The valve 106 controls nitrogen flow from the pressure source 26 to manifold 38. When the valve 106 is actuated, the manifold 38 is cut off from the pressure source 26, and pressure in the manifold 38 is vented to the atmosphere. Then, the selected reservoir 14a–14n may be removed for filling or replacement.

Similarly, a valve 108 is positioned in line 30b, for refilling or replacing the reservoirs 16a–16n. After the valve 108 is actuated, the corresponding valve 36a–36n is actuated, thus venting the selected reservoir 16a–16n to the atmosphere, so that it may be removed for filling or replacement.

As stated above, cross-contamination between amino acids must be avoided if a peptide chain having the appropriate sequence is to be built. For this reason, the reagent reservoirs 16a–16n are connected upstream from the amino acid reservoirs 14a–14n along the common transfer line 20. Thus when reagents and/or solvents are transferred to the vessel after the selected amino acid is transferred, any residual amino acid remaining in the main line 20 is flushed into the vessel by flow of the solvents and/or reagents through the line 20.

The pressure in the system 10 remains constant even when solvents of varying vapor pressure are used. This is because the regulator 28 regulates total system pressure, which includes vapor pressure as well as a component from the pressure source 26. An accurate delivery of solvents, reagents and amino acids can thus be assured because the system is maintained at the constant reference pressure.

The system 10 is preferably equipped with a yield monitor, indicated generally at 120, to assess the completeness of each amino acid addition. The yield may be assessed by the use of a covalent reversible monitoring agent which binds reversibly to the free amino termini of those peptide chains that did not react with the last preceding amino acid added to the peptide chains.

A monitoring method using such an agent proceeds as follows. After each addition of a blocked amino acid to the anchored peptide chains, but before deblocking to receive the next amino acid to be added to the peptide chain, the matrix M containing the anchored peptide chains is reacted with the monitoring agent. The contents of the vessel are then thoroughly washed, and the monitoring agent is selectively removed from those peptide chains to which it is attached, under conditions that leave intact the blocked ends of the peptide chains that reacted with the last preceding amino acid, and which leave intact the peptide chains themselves. The cleaved monitoring agent is then transferred to a sample cell 122 in a monitor 120, where the concentration of the monitoring agent is measured.

More specifically, the monitor 120 connects to the rest of the system 10 through the valve 92. Valve 92 in its deactuated, or normal connection, places the monitor 120 in communication with the valve 82. To effect the transfer to the sample cell 122, the valve 82 is actuated, thereby connecting the vesel 12 to the cell 122 by way of valve 66, line 68, and valve 92. The transfer is driven by a pressure differential between the sample cell 122, which is at atmospheric pressure, and the vessel 12, which is at the system pressure P. A detector 124, such as a spectrophotometer which senses the absorbance of the contents of the cell 122, thereby measures the concentration of the monitoring agent therein. The amount of monitoring agent is thus quantitated and the yield in the previous amino-acid addition step determined by the processor 24, which compares this value to the desired yield. This yield corresponds directly to the number of free unreacted amino termini on the anchored peptide chains, and thus is representative of the portion of the peptide chains that did not react in the last preceding amino acid addition. If the yield is not high enough, the previous amino acid addition may be repeated until the desired yield is attained. If successive repetitions do not improve the yield, the entire synthesis may be terminated, or a second blocking group may be added to permanently block the unreacted amino termini of these peptide chains, and prevent further additions to them. Thus it is easier to separate these shorter peptide chains from the peptide chains of interest than to separate the peptide chains differing by only one amino acid residue from the peptide chains of interest.

The covalent-and-reversible monitoring agents we use are a class of trityl (triphenyl methyl) compounds, such as trityl chloride, dimethoxy trityl chloride, monomethoxy trityl chloride, and trimethoxy trityl chloride. They are specific for free amino groups and do not react with the blocked amino acid side groups. Hence, the background noise of the monitoring is very low, and remains low even as the peptide chain length increases. These compounds have high extinction coefficients which make monitoring very sensitive. The presence of the monitoring agent is easily detected by absorbance in a spectrophotometer at the appropriate wavelength, thus making the monitoring simple and economical.

The following is a specific reaction protocol using trityl chloride as a representative monitoring agent.

(A) REACT THE SOLID PHASE WITH AN EXCESS OF TRITYL CHLORIDE

At the end of each addition of a blocked amino acid, but before deblocking, the contents of the vessel 12 are washed twice with dimethylformamide (DMF). Then, a solution of 5% trityl chloride and 5% diisopropyl ethylamine in DMF is added to the vessel 12 and the contents are mixed for 15 minutes at room temperature.

(B) REMOVE BOUND TRITYL GROUPS FROM THE SOLID PHASE

The contents of the vessel 12 are then washed twice with DMF to remove any excess, unreacted trityl chloride. All trityl groups left in the vessel 12 are thus bound to the free amino groups on the matrix M. Specifically, they are bound to the termini of the peptide chains that did not react with the last preceding amino acid. The trityl groups bound to the matrix M in the vessel is then removed by adding a solution of 7% Trichloroacetic Acid in Dichloromethane to the solid phase and allowing it to react for 10 minutes with gentle mixing. Under these conditions, the trityl-amino bond is broken, forming soluble trityl carbonium ions.

(C) QUANTITATE THE AMOUNT OF SOLUBLE TRITYL GROUPS

The liquid phase is then transferred to the monitor as described previously, and the level of the trityl carbonium ions is quantitated by measuring the absorbance at 259 nanometers. In the above trichloroacetic acid—dichloromethane solvent, the trityl moiety has a molar extinction coefficient on the order of $10^3$. Thus, the yield at each amino acid addition step in the reaction vessel 12 can be determined with a high degree of accuracy and without significantly destroying the peptide chains that were synthesized correctly.

If dimethoxy trityl chloride is used, it can be detected spectrophotometrically at visible light wavelengths, which makes detection simpler and less expensive. The dimethoxy trityl moiety has a molar extinction coefficient on the order of $10^5$, which makes it a more sensitive monitoring agent than trityl chloride.

Thus, we have provided an improved system for synthesizing peptides wherein the transfers of amino acids, reagents and solvents from their respective reservoirs to the reaction vessel are accomplished quickly, easily, and economically by volume displacement and pressure equilibrium. Cross-contamination of reagents in the transfer lines and valves is minimal. The system can be easily optimized for producing a high yield at each amino acid addition step, and the yield at each step can be monitored easily and effectively to facilitate the production of peptides having a high ultimate yield.

It will thus be seen that the objects set forth above, among those made apparent from the preceding description, are efficiently attained. Also, certain changes may be made in carrying out the above method and in the above construction without departing from the scope of the invention.

For example, the reference pressure may be momentarily increased when the vessel 12 is to be flushed, for faster removal of waste and washes. Also, the monitor 120 may be adapted to accomodate other monitoring methods.

Therefore, it is intended that all matter contained in the above description or shown in the accompanying drawing be interpreted as illustrative and not in a limiting sense.

It is also to be understood that the following claims are intended to cover all of the generic and specific features of the invention herein described.

What is claimed as new and desired to be secured by Letters Patent of the United States is:

1. A system for the solid-phase synthesis of peptides by successive amino-acid additions to peptide chains anchored to a solid support matrix, the system comprising:
A. a reaction vessel enclosing the solid support matrix and comprising
   (1) a single port for bidirectional flow therethrough into and out of the vessel, and
   (2) a porous filter positioned in the vessel adjacent the single port for retaining the solid support matrix in the reaction vessel while allowing passage of fluids from the vessel;
B. a plurality of reservoirs, each containing a solvent or reagent, or an amino acid used for the synthesis of said peptide;
C. means for supplying a reference pressure to the vessel and the reservoirs and the rest of the system;
D. means for removing a predetermined continuously variable volume of gas from the vessel; and
E. means for displacing said removed volume of gas with a predetermined volume of a selected solvent, reagent or amino acid from one of said reservoirs in response to the difference in pressure between the reference pressure and the pressure in the vessel.

2. A system as described in claim 1 and further including a processor for automatically controlling the supplying means, the removing means and the displacing means.

3. A system as described in claim 1 and further including exhaust means for emptying the reaction vessel.

4. A system as described in claim 1 and further including means for monitoring the yield of each amino acid addition.

5. A system as described in claim 4 and further including means for repeating the previous amino acid addition before proceeding to the next successive addition when the yield monitoring means detects a yield that is below a predetermined level.

6. A system for the solid-phase synthesis of peptides by successive amino-acid additions to peptide chains anchored to a solid support matrix, the system comprising:
A. a reaction vessel enclosing a solid support matrix and comprising:
   (1) a single port for bidirectional flow therethrough into and out of the vessel, and
   (2) a porous filter positioned in the vessel adjacent the single port for retaining the solid support matrix while allowing passage of fluids from the vessel;
B. a plurality of reservoirs, each containing a solvent or regent, or an amino acid used for the synthesis of said peptide;
C. transfer lines connecting said reaction vessel to said reservoirs;
D. means for maintaining a reference pressure in the system;
E. means for removing a predetermined, continuously variable volume of gas from said reaction vessel comprising syringe means connectable to said reaction vessel; and
F. means for transferring a measured, variable volume of a liquid, proportional to said volume of gas, from a selected one of said reservoirs to the reaction vessel through the transfer lines, said transferring means comprising:
   (1) valve means operable between
      (a) a first state in which said reaction vessel is closed to said reservoirs and said reference pressure and said reaction vessel is connected to said syringe means, and
      (b) a second state in which said reaction vessel is closed to said syringe means and said selected reservoir is connected to said reaction vessel,
   whereby a transfer of liquid from said reservoir to said reaction vessel occurs by
   (1) operating the syringe means while the valve means is in its first state to remove the predetermined volume of gas from said reaction vessel, and subsequently,
   (2) operating the valve means in its second state so that liquid from said reservoir is transferred to said reaction vessel until the pressure in the reaction vessel reaches the reference pressure.

* * * * *